United States Patent
Ziegler

(10) Patent No.: US 9,051,540 B2
(45) Date of Patent: Jun. 9, 2015

(54) APPARATUS AND METHOD FOR TREATMENT OF VOLATILE ORGANIC COMPOUNDS IN AIR EMISSIONS PRODUCED DURING FERMENTATION PROCESSES

(75) Inventor: Allen Ziegler, Littleton, CO (US)

(73) Assignee: Resonaut Biosciences, LLC, Littleton, CO (US)

( * ) Notice: Subject to any disclaimer, the term of this patent is extended or adjusted under 35 U.S.C. 154(b) by 230 days.

(21) Appl. No.: 13/517,969

(22) PCT Filed: Dec. 21, 2010

(86) PCT No.: PCT/US2010/061554
§ 371 (c)(1),
(2), (4) Date: Sep. 19, 2012

(87) PCT Pub. No.: WO2011/079120
PCT Pub. Date: Jun. 30, 2011

(65) Prior Publication Data
US 2013/0009092 A1    Jan. 10, 2013

Related U.S. Application Data

(60) Provisional application No. 61/289,606, filed on Dec. 23, 2009.

(51) Int. Cl.
| | | |
|---|---|---|
| B01D 53/02 | (2006.01) | |
| B01D 53/56 | (2006.01) | |
| B01J 8/00 | (2006.01) | |
| B01D 53/14 | (2006.01) | |
| C01B 7/00 | (2006.01) | |
| C01B 11/02 | (2006.01) | |
| C12M 1/00 | (2006.01) | |
| B01D 53/72 | (2006.01) | |
| C12P 7/06 | (2006.01) | |

(52) U.S. Cl.
CPC ............... *C12M 47/18* (2013.01); *B01D 53/72* (2013.01); *B01D 2251/108* (2013.01); *B01D 2257/504* (2013.01); *B01D 2257/708* (2013.01); *C12P 7/06* (2013.01); *Y02E 50/16* (2013.01); *Y02E 50/17* (2013.01)

(58) Field of Classification Search
USPC .................. 423/245.1, 254.1, 245.2, 462, 477
See application file for complete search history.

(56) References Cited

U.S. PATENT DOCUMENTS

2004/0237782 A1 * 12/2004 Decker ........................... 95/211
2012/0148477 A1 * 6/2012 Rosenblatt et al. ........... 423/477

*Primary Examiner* — James McDonough
(74) *Attorney, Agent, or Firm* — Smyrski Law Group, A P.C.

(57) ABSTRACT

A method of reducing volatile organic compounds produced during a fermentation process includes (a) producing a volatile organic compound during a fermentation process, (b) generating $ClO_2$ gas, (c) dissolving the $ClO_2$ gas to form a $ClO_2$ solution, and (d) introducing an aqueous $ClO_2$ solution into said volatile organic compound wherein introducing said $ClO_2$ solution reduces concentration of said volatile organic compounds. Another method includes (a) producing a volatile organic compound during a fermentation process, and (b) introducing $ClO_2$ having an efficiency as $ClO_2$ of at least about 90% into the volatile organic compound wherein introducing said $ClO_2$ solution reduces concentration of said volatile organic compounds. An apparatus for treating volatile organic compounds produced during a fermentation process comprises a $ClO_2$ generator fluidly connected to a batch tank, fluidly connected to a volatile organic compound producing fermentation vessel.

26 Claims, 1 Drawing Sheet

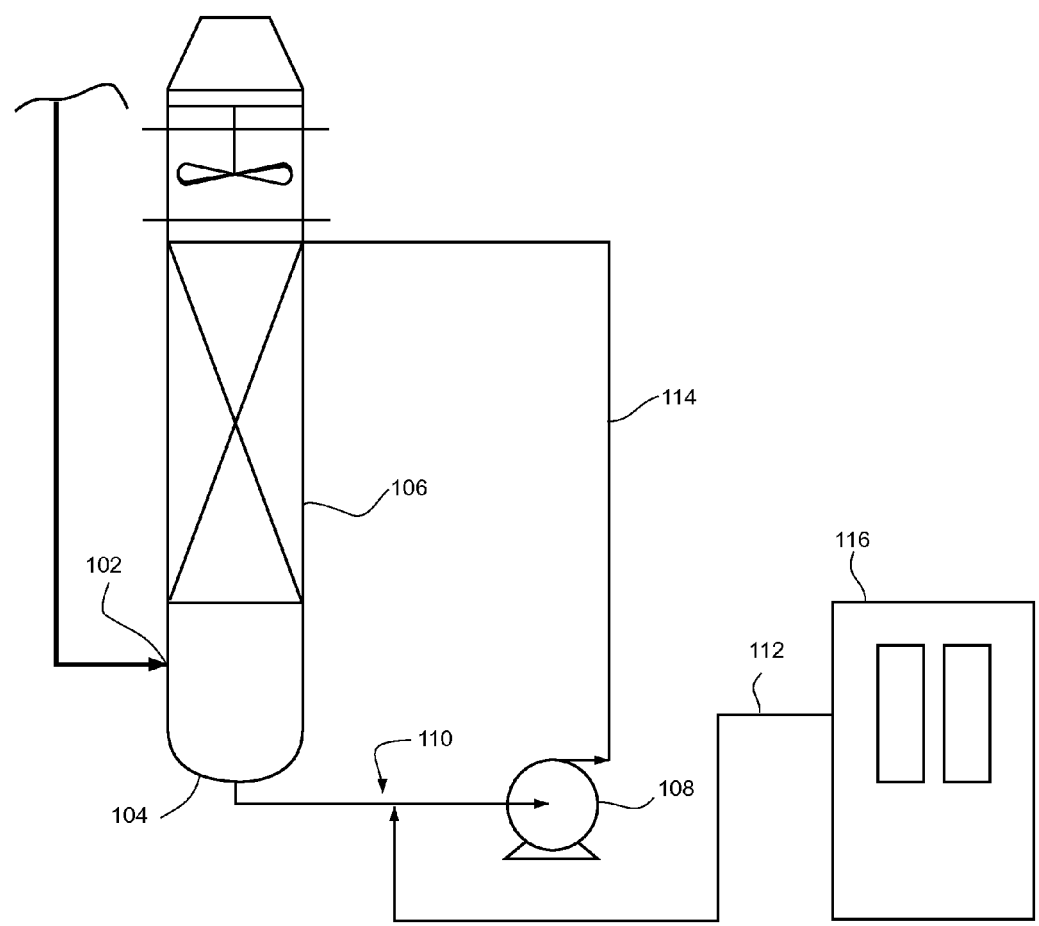

APPARATUS AND METHOD FOR TREATMENT OF VOLATILE ORGANIC COMPOUNDS IN AIR EMISSIONS PRODUCED DURING FERMENTATION PROCESSES

The present application is a U.S. National Stage Filing pursuant to 35 U.S.C. §371 based on and claiming priority to PCT Application PCT/US2010/061554, entitled "Apparatus and Method for Treatment of Volatile Organic Compounds in Air Emissions Produced During Fermentation Processes," inventor Allen Ziegler, filed 21 Dec. 2010, which claims priority to U.S. Provisional Patent Application 61/289,606, filed Dec. 23, 2009, and the disclosures of both applications are incorporated herein by reference.

FIELD OF THE INVENTION

Generally, the technical field involves controlling volatile organic compounds (VOC's) that are produced during microbial fermentation processes. Specifically, it is a method of reducing the concentration of VOC's emitted into the air during ethanol production.

BACKGROUND OF THE INVENTION

Fermentation is a process where microorganisms convert carbohydrates, such as sugar, into alcohols or acids. Microorganisms, such as yeast, fungi and bacteria, are used to produce a number of fermentation products, such as industrial grade ethanol, distilled spirits, beer, wine, pharmaceuticals and nutraceuticals (foodstuff that provides health benefits, such as fortified foods and dietary supplements). The microorganisms are combined in an aqueous solution with fermentable sugars. The microorganisms consume the sugars, converting them into aliphatic alcohols, such as ethanol.

The fermentation process produces a great deal of carbon dioxide that evolves from the top of the fermentor. In addition to carbon dioxide, other problematic gases are produced in the fermentation process. These gases are often classified as volatile organic compounds (VOC's). VOC emissions are regulated by the government, which means fermentation facility can only emit a limited quantity of VOC's into the air. The two primary regulated VOC's are acetyl aldehyde an acrolein. Other VOC's compounds are produced in minimal quantities or not regulated at all. Examples of these other VOC's include, ethyl acetate, ethanol, isoamyl alcohol, acetic acid, furaldehyde, formaldehyde, and formic acid. In response to the regulations discussed above, fermentation facilities, such as ethanol plants, attempt to limit or reduce their VOC output.

Most facilities currently employ a carbon dioxide scrubber to capture the carbon dioxide and VOC's exiting the fermentor(s). The carbon dioxide scrubber flows a water solution counter current to the gases at a rate between 25 to 300 gallons per minute. This solubilizes the gases in a water solution. Reducing agents, such as sodium bisulfite or ammonium bisulfite, are then injected into the water solution. These reducing agents react with the VOC's to reduce the regulated compounds into non-regulated compounds.

Chlorine dioxide ($ClO_2$) has many industrial and municipal uses. When produced and handled properly, $ClO_2$ is an effective and powerful biocide, disinfectant and oxidizer.

$ClO_2$ has been used as a disinfectant in the food and beverage industries, wastewater treatment, industrial water treatment, cleaning and disinfections of medical wastes, textile bleaching, odor control for the rendering industry, circuit board cleansing in the electronics industry, and uses in the oil and gas industry. It is an effective biocide at low concentrations and over a wide pH range. $ClO_2$ is desirable because when it reacts with an organism in water, it reduces to chlorite ion and then to chloride, which studies to date have shown does not pose a significant adverse risk to human health.

$ClO_2$ is, however, unstable in the gas phase and will readily undergo decomposition into chlorine gas ($Cl_2$), oxygen gas ($O_2$), and heat. The high reactivity of $ClO_2$ generally requires that it be produced and used at the same location.

Recently, it was discovered that chlorine dioxide effectively reduce undesirable microorganisms during propagation, conditioning and/or fermentation while encouraging propagation and/or conditioning of the desirable microorganisms and increase their efficiency in fermentation. This is discussed in co-owned U.S. patent application Ser. No. 11/626,272, filed Jan. 23, 2007, entitled "Apparatus and Method for Treatment of Microorganisms During Propagation, Conditioning and Fermentation," which claims priority benefits from U.S. Provisional Patent Application Ser. No. 60/775,615, filed Feb. 22, 2006, entitled "Apparatus and Method for Treatment of Yeast During Propagation, Conditioning and Fermentation." Both of these applications are hereby incorporated by reference in their entirety.

Accordingly, it would be desirable to provide a less costly and more effective method of oxidizing and thereby reducing VOC's produced during the fermentation processes.

SUMMARY OF THE INVENTION

A method for treating volatile organic compounds produced during a fermentation process comprises (a) producing a volatile organic compound during a fermentation process (b) generating $ClO_2$ gas, (c) dissolving the $ClO_2$ gas to form a $ClO_2$ solution, and (d) introducing an aqueous $ClO_2$ solution into the volatile organic compound wherein introducing said $ClO_2$ solution reduces concentration of said volatile organic compounds. These steps can be performed sequentially or in a different order.

The $ClO_2$ gas can be generated by reacting chlorine gas with water and then adding sodium chlorite. Alternatively the $ClO_2$ gas could be generated by reacting sodium hypochlorite with an acid and then adding sodium chlorite. The $ClO_2$ gas can also be generated by reacting sodium chlorite and hydrochloric acid. The $ClO_2$ gas can also be generated using electrochemical cells and sodium chlorate or sodium chlorite. Equipment-based generation could also be used to create $ClO_2$ gas using sodium chlorate and hydrogen peroxide.

In one embodiment, the $ClO_2$ solution has a concentration of between about one and about 150 mg/L. In one embodiment the $ClO_2$ solution has an efficiency as $ClO_2$ in the stream of at least about 90%. As used in this application "to have an efficiency as $ClO_2$ of at least about 90%" means that at least about 90% of the $ClO_2$ solution or $ClO_2$ gas is in the form of $ClO_2$.

The volatile organic compound can be acetyl aldehyde, acrolein, ethyl acetate, ethanol, or isoamyl alcohol.

Another method for treating volatile organic compounds produced during a fermentation process comprises (a) producing a volatile organic compound during a fermentation process, and (b) introducing $ClO_2$ having an efficiency as $ClO_2$ of at least about 90% into said volatile organic compound wherein introducing said $ClO_2$ solution reduces concentration of said volatile organic compounds. These steps can be performed sequentially or in a different order.

The $ClO_2$ having an efficiency as $ClO_2$ in the stream of at least about 90% can be produced by equipment or non-equipment based methods. Examples of non-equipment based methods of $ClO_2$ generation include dry mix chlorine dioxide packets that include both a chlorite precursor packet and an acid activator packet. Equipment-based methods include using electrochemical cells with sodium chlorate or sodium chlorite, and a sodium chlorate/hydrogen peroxide method.

In one embodiment, the $ClO_2$ solution is in the form of an aqueous solution having a concentration of between about one and about 150 mg/L. In another embodiment the $ClO_2$ is in a gaseous form.

The volatile organic compound can be acetyl aldehyde, acrolein, ethyl acetate, ethanol, or isoamyl alcohol.

An apparatus for treating volatile organic compounds produced during a fermentation process comprises a $ClO_2$ generator, a batch tank and a volatile organic compound producing fermentation vessel. The $ClO_2$ generator comprises an inlet for introducing at least one chlorine-containing feed chemical and an outlet for exhausting a $ClO_2$ gas stream from the generator. The batch tank is fluidly connected to the $ClO_2$ generator outlet and receives the $ClO_2$ gas stream from the $ClO_2$ generator outlet. The batch tank comprises an inlet for introducing a water stream and an outlet for exhausting an aqueous $ClO_2$ solution from the batch tank.

The batch tank preferably has an inlet for introducing a water stream and an outlet for exhausting an aqueous $ClO_2$ solution. In one preferred embodiment, the exhausted $ClO_2$ solution is dosed to have a concentration between about one and about 150 mg/L.

In one embodiment the volatile organic compound producing fermentation vessel is a carbon dioxide scrubber. In this embodiment the volatile organic compound evolves from the top of the fermentor, into the carbon dioxide scrubber and the aqueous $ClO_2$ solution in introduced at the bottom of the carbon dioxide scrubber.

The volatile organic compound can be acetyl aldehyde, acrolein, ethyl acetate, ethanol, or isoamyl alcohol.

BRIEF DESCRIPTION OF THE DRAWINGS

FIG. 1 is a schematic of VOC treatment equipment with an integrated $ClO_2$ system in accordance with one embodiment.

DETAILED DESCRIPTION OF PREFERRED EMBODIMENT(S)

The current disclosure relates to a method for treating volatile organic compounds (VOC's) produced during a fermentation process. Specifically the current disclosure relates to methods for reducing concentration of VOC's produced during ethanol production.

The production of fuel ethanol by yeast fermentation is used as an example. However, this is merely one illustration and should not be understood as a limitation. Other fermentation products could include distilled spirits, beer, wine, pharmaceuticals, pharmaceutical intermediates, baking products, nutraceuticals (foodstuff that provides health benefits, such as fortified foods and dietary supplements), nutraceutical intermediates and enzymes. The current method could also be utilized to treat yeast used in the baking industry. Other fermenting microorganisms could also be substituted such as the fungi and bacteria typically used in cellulosic ethanol production, *Trichoderma reesei*, *Trichoderma viride*, and *Clostridium Ijungdahlii*.

The fermentation process begins with the preparation of a fermentable carbohydrate. In ethanol production, corn is one possible fermentable carbohydrate. Other carbohydrates including cereal grains and cellulose-starch bearing materials, such as wheat or milo, could also be substituted. Cellulosic biomass such as straw and cornstalks could also be used. Cellulosic ethanol production has recently received attention because it uses readily available nonfood biomass to form a valuable fuel. Sugar could also be used. Sugar has also recently received attention as another potential starting material for ethanol production.

In corn-based ethanol production the corn is ground into a fine powder called meal. The meal is then mixed with water and enzymes, such as alpha-amylase, and passed through a cooker in order to liquefy the starch. A product known as corn mash results.

A secondary enzyme, such as glucoamylase, will also be added to the mash to convert the liquefied starch into a fermentable sugar. The glucoamylase cleaves single molecules of glucose from the short chain starches, or dextrins. The glucose molecules can then be converted into ethanol during fermentation.

Yeast, small microorganisms capable of fermentation, will also be added to the corn mash. Yeast are fungi that reproduce by budding or fission. One common type of yeast is *Saccharomyces cerevisia*, the species predominantly used in baking and fermentation. Non-*Saccharomyces* yeasts, also known as non-conventional yeasts, are naturally occurring yeasts that exhibit properties that differ from conventional yeasts. Non-conventional yeasts are utilized to make a number of commercial products such as amino acids, chemicals, enzymes, food ingredients, proteins, organic acids, nutraceuticals, pharmaceuticals, cosmetics, polyols, sweeteners and vitamins. Some examples of non-conventional yeasts include *Kuyberomyces lactis, Yarrowia lipolytica, Hansenula polymorpha* and *Pichia pastoris*. The current methods and apparatus are applicable to intermediates and products of both *Saccharomyces* and non-conventional yeast.

Most of the yeast used in fuel ethanol plants and other fermentation processes are purchased from manufacturers of specialty yeast. The yeast are manufactured through a propagation process and usually come in one of three forms: yeast slurry, compressed yeast or active dry yeast. Propagation involves growing a large quantity of yeast from a small lab culture of yeast. During propagation the yeast are provided with the oxygen, nitrogen, sugars, proteins, lipids and ions that are necessary or desirable for optimal growth through aerobic respiration.

Once at the distillery, the yeast may undergo conditioning. The objectives of both propagation and conditioning are to deliver a large volume of yeast to the fermentation tank with high viability, high budding and a low level of infection by other microorganisms. However, conditioning is unlike propagation in that it does not involve growing a large quantity from a small lab culture. During conditioning, conditions are provided to re-hydrate the yeast, bring them out of hibernation and allow for maximum anaerobic growth and reproduction.

Following propagation or conditioning, the yeast enter the fermentation process. The glucoamylase enzyme and yeast are often added into the fermentation tank through separate lines as the mash is filling the fermentation tank. This process is known as simultaneous saccharification and fermentation or SSF. The yeast produce energy by converting the sugars, such as glucose molecules, in the corn mash into carbon dioxide and ethanol.

The fermentation mash, now called "beer" is distilled. This process removes the 190 proof ethanol, a type of alcohol, from the solids, which are known as whole stillage. These solids are then centrifuged to get wet distillers grains and thin stillage. The distillers grains can be dried and are highly valued livestock feed ingredients known as dried distillers grains (DDGS). The thin stillage can be evaporated to leave a syrup. After distillation, the alcohol is passed through a dehydration system to remove remaining water. At this point the product is 200 proof ethanol. This ethanol is then denatured by adding a small amount of denaturant, such as gasoline, to make it unfit for human consumption.

The propagation, conditioning and fermentation processes can be carried out using batch and continuous methods. The batch process is used for small-scale production. Each batch is completed before a new one begins. The continuous fermentation method is used for large-scale production because it produces a continuous supply without restarting every time. The current method and apparatus are effective for both methods.

The fermentation process produces a great deal of carbon dioxide that evolves from the top of the fermentor. In addition to carbon dioxide, other problematic gases are produced in the fermentation process. These gases are often classified as volatile organic compounds (VOC's). VOC emissions are regulated by the government, which means fermentation facility can only emit a limited quantity of VOC's into the air. The two primary regulated VOC's are acetyl aldehyde an acrolein. Other VOC's compounds are produced in minimal quantities or not regulated at all. Examples of these other VOC's include, ethyl acetate, ethanol, isoamyl alcohol, acetic acid, furaldehyde, formaldehyde, and formic acid. In response to the regulations discussed above, fermentation facilities, such as ethanol plants, attempt to limit or reduce their VOC output.

Most facilities currently employ a carbon dioxide scrubber or RTO (Regenerative Thermal Oxidizer) to capture the carbon dioxide and VOC's exiting the fermentor(s). The carbon dioxide scrubber flows a water solution counter current to the gases at a rate between 25 to 300 gallons per minute. This solubilizes the gases in a water solution. Reducing agents, such as sodium bisulfite or ammonium bisulfite, are then injected into the water solution. These reducing agents react with the VOC's to reduce the regulated compounds into non-regulated compounds.

$ClO_2$ solution has many uses in disinfection, bleaching and chemical oxidation. $ClO_2$ can be added during a fermentation process to reduce or eliminate volatile organic compounds. This $ClO_2$ can be added as an aqueous solution or a gas. In one embodiment the $ClO_2$ has an efficiency as $ClO_2$ in the stream of at least about 90%. Adding $ClO_2$ having a known purity allows for addition of a controlled amount of $ClO_2$.

The current method for treating volatile organic compounds produced during a fermentation process comprises (a) producing a volatile organic compound during a fermentation process (b) generating $ClO_2$ gas, (c) dissolving the $ClO_2$ gas to form a $ClO_2$ solution, and (d) introducing an aqueous $ClO_2$ solution into the volatile organic compound wherein introducing said $ClO_2$ solution reduces concentration of said volatile organic compounds. These steps can be performed sequentially or in a different order.

Another method for treating volatile organic compounds produced during a fermentation process comprises (a) producing a volatile organic compound during a fermentation process, and (b) introducing $ClO_2$ having an efficiency as $ClO_2$ of at least about 90% into said volatile organic compound wherein introducing said $ClO_2$ solution reduces concentration of said volatile organic compounds. These steps can be performed sequentially or in a different order.

Examples of the volatile organic compound can be acetyl aldehyde, acrolein, ethyl acetate, ethanol, isoamyl alcohol acetic acid, furaldehyde, formaldehyde or formic acid. The most commonly regulated volatile organic compounds are acetyl alcohol and acrolein.

The $ClO_2$ reduces to form chlorite ion and then further reduces to form chloride ion and/or salt. The reduction from $ClO_2$ to chloride ion happens quickly and is indeterminate compared to the background residual already present. The chloride ion is a non-hazardous byproduct unlike those created by many antibiotics. Studies to date have shown that chloride ion does not pose a significant adverse risk to human health.

Since $ClO_2$ gas can decompose explosively, it is typically produced on-site. There are a number of methods of producing $ClO_2$ gas having a known purity, which are known to persons familiar with the technology involved here. One or more of these methods can be used. $ClO_2$ gas can be produced using electrochemical cells and a sodium chlorite or sodium chlorate solution. An equipment based sodium chlorate/hydrogen peroxide method also exists. Alternatively, non-equipment based binary, multiple precursor dry or liquid precursor technologies can be used. Examples of non-equipment based methods of $ClO_2$ generation include dry mix chlorine dioxide packets that include both a chlorite precursor packet and an acid activator packet. Other such processes include, but are not limited to, acidification of sodium chlorite, oxidation of chlorite by chlorine, oxidation of chlorite by persulfate, use of acetic anhydride on chlorite, use of sodium hypochlorite and sodium chlorite, use of dry chlorine/chlorite, reduction of chlorates by acidification in the presence of oxalic acid, reduction of chlorates by sulfur dioxide, and the ERCO R-2®, R-3®, R-5®, R-8®, R-10® and R-11® processes, from which $ClO_2$ is generated from $NaClO_3$ in the presence of NaCl and $H_2SO_4$ (R-2 and R-3 processes), from $NaClO_3$ in the presence of HCl (R-5 process), from $NaClO_3$ in the presence of $H_2SO_4$ and $CH_3OH$ (R-8 and R-10 processes), and from $NaClO_3$ in the presence of $H_2O_2$ and $H_2SO_4$ (R-11 process).

Here, three methods will illustrate some possibilities. In the first method, chlorine reacts with water to form hypochlorous acid and hydrochloric acid. These acids then react with sodium chlorite to form chlorine dioxide, water and sodium chloride. In a second method, sodium hypochlorite is combined with hydrochloric or other acid to form hypochlorous acid. Sodium chlorite is then added to this reaction mixture to produce chlorine dioxide. The third method combines sodium chlorite and sufficient hydrochloric acid. In one embodiment the $ClO_2$ gas produced is between 0.0005 and 5.0% by weight in air.

The $ClO_2$ gas is dissolved in a solvent in order to create a $ClO_2$ solution. $ClO_2$ gas is readily soluble in water. In one embodiment the water and $ClO_2$ gas are combined in quantities that create a solution with a concentration of about 3000 mg/L. In one embodiment the 3000 mg/L aqueous chlorine dioxide solution is dosed at the bottom or the carbon dioxide scrubber at a rate of about one to about 150 mg/L.

Pure or substantially pure $ClO_2$ is desirable because it allows the user to precisely maintain the amount of $ClO_2$ added to the yeast. (The single term "pure" will be used hereinafter to mean either pure or substantially pure.) If too little $ClO_2$ is added it will not effectively reduce volatile organic compound concentration. If too much $ClO_2$ is added it wastes resources and can negatively affect other aspects of the fermentation process. If either of these situations occurs, the addition of $ClO_2$ will not result in efficient reduction of volatile organic compound concentration. Addition of pure $ClO_2$ allows the user to carefully monitor and adjust the amount of $ClO_2$ added.

Plant scale evaluations have determined that volatile organic compound concentration can be reduced by applying chlorine dioxide solution. Evaluations were carried out at an ethanol production facility. A chlorine dioxide generator capable of dosing up to 60 mg/L of chlorine dioxide at a flow rate of 45 gallons per minute. The chlorine dioxide generator utilized a chlorine dioxide solution with a concentration of 300 mg/L. The pump skid contained a built in draw down cylinder to confirm feed rate and the chlorine dioxide concentration was checked via spectrophotometer. The dosage point was the incoming water located at the bottom of the carbon dioxide scrubber.

The volatile organic compound emissions from the carbon dioxide scrubber were analyzed using a gas chromatograph. The test coincided with the peak of the fermentation cycle and/or maximum volatile organic compound output. A control was conducted without addition of chlorine dioxide for comparison.

The following tables show the results of the gas chromatograph analysis for the evaluation plant.

TABLE 1

Total Volatile Organic Compound Concentration in Fermentation Emissions without Chlorine Dioxide and When Treated With 60 mg/L Chlorine Dioxide

| Time | With Chlorine Dioxide Total VOC (mg/L) | Without Chlorine Dioxide Total VOC (Estimated) (mg/L) |
| --- | --- | --- |
| 5:20 PM | 74.1 | 82-100 |
| 5:30 PM | 72.3 | 82-100 |
| 5:40 PM | 70.2 | 82-100 |
| 5:52 PM | 67.9 | 82-100 |
| 5:58 PM | 66.7 | 82-100 |
| 6:00 PM | 65.4 | 82-100 |

TABLE 2

Specific Volatile Organic Compound Output Concentrations in Fermentation Emissions without Chlorine Dioxide and When Treated With 60 mg/L Chlorine Dioxide

| Volatile Organic Compound | With Chlorine Dioxide | Without Chlorine Dioxide |
| --- | --- | --- |
| Acetyl aldehyde | 14.99 ppm (0.51 lb/hr) | 24.11 ppm (0.82 lb/hr) |
| Ethyl acetate | 7.92 ppm (0.53 lb/hr) | 8.95 ppm (0.61 lb/hr) |
| Methanol | 0.23 ppm (0.01 lb/hr) | 0.23 ppm (0.01 lb/hr) |
| Ethanol | 1.39 ppm (0.05 lb/hr) | 2.64 ppm (0.09 lb/hr) |
| Isoamyl alcohol | 0.08 ppm (0.01 lb/hr) | 2.18 ppm (0.15 lb/hr) |
| Acetic acid | 7.72 ppm (0.36 lb/hr) | 6.18 ppm (0.29 lb/hr) |
| Furaldehyde | 0.08 ppm (0.01 lb/hr) | 0.08 ppm (0.01 lb/hr) |
| Formaldehyde | 0.06 ppm (0.00 lb/hr) | 0.00 ppm (0.00 lb/hr) |
| Formic acid | 4.91 ppm (0.11 lb/hr) | 4.91 ppm (0.11 lb/hr) |
| Total Non-Methane Volatile Organic Compound | 1.58 ppm (3.69 lb/hr) (16.15 tons/year) | 2.09 ppm (4.74 lb/hr) (20.76 tons/year) |

As shown in Tables 1-2, chlorine dioxide demonstrated the ability to oxidize certain problematic volatile organic compounds, such as acetyl aldehyde, ethyl acetate, ethanol, and isoamyl alcohol. Specifically, chlorine dioxide can be used to oxidize acrolein into acrylic acid and acetyl aldehyde into acetic acid. Acrolein and acetyl aldehyde are the primary regulated volatile organic compounds. The oxidation of acetyl aldehyde to acetic acid, another volatile organic compound, is not problematic due to the unregulated status of acetic acid.

Addition of chlorine dioxide was able to reduce volatile organic compounds in the range of 9.6 to about 34.6% depending on the dosage rate. This reduction in volatile organic compounds is sufficient to comply with regulatory rules because regulations only require that volatile organic compound emissions be reduced, not eliminated.

$ClO_2$ could also be used to control volatile organic compounds in the production of cellulosic ethanol. Cellulosic ethanol is a type of ethanol that is produced from cellulose, as opposed to the sugars and starches used in producing carbohydrate based ethanol. Cellulose is present in non-traditional biomass sources such as switch grass, corn stover and forestry. This type of ethanol production is particularly attractive because of the large availability of cellulose sources. Cellulosic ethanol, by the very nature of the raw material, introduces higher levels of contaminants and competing microorganism into the fermentation process.

The current apparatus for carrying out the fermentation process with an integrated $ClO_2$ system has a $ClO_2$ generator. The $ClO_2$ generator has an input for electricity. There is also an inlet for at least one chlorine containing chemical. There are three different types of chemical feed systems: a vacuum system, a pressure system and a combination system. Many types of feed systems can be employed to deliver chemicals in a fluid state. Chlorine gas, for example, can be added by a vacuum or combination feed system. The $ClO_2$ generator should also have an outlet for exhausting a $ClO_2$ gas stream from the generator.

A batch tank that receives the $ClO_2$ gas stream is fluidly connected to the $ClO_2$ generator outlet. In the batch tank the $ClO_2$ gas is dissolved in water to form a $ClO_2$ solution. The batch tank has an inlet for introducing a water stream. The water stream and the $ClO_2$ gas stream are combined to form a $ClO_2$ solution. The concentration of the $ClO_2$ solution in the batch tank can vary across a wide range. Concentrations of up to about 5,000 mg/L can be achieved and concentrations of up to about 8,000 mg/L can be achieved with additional equipment. The $ClO_2$ solution is then exhausted from the batch tank through an outlet at a specified dosage rate to create a solution of the desired concentration. In one embodiment the dosed $ClO_2$ solution, has a concentration of between about one and about 150 mg/L. In one embodiment, the exiting $ClO_2$ solution has an efficiency as $ClO_2$ in the stream of at least about 90%.

A volatile organic compound producing fermentation vessel is fluidly connected to the batch tank via the $ClO_2$ solution outlet. The volatile organic compound producing fermentation vessel is any vessel used during fermentation that emits volatile organic compounds. In one example the volatile organic compound producing vessel is a carbon dioxide scrubber. The volatile organic compound flows off the top of the fermentor into the carbon dioxide scrubber system. The batch tank is fluidly connected to the carbon dioxide scrubber system. The batch tank introduces the aqueous chlorine dioxide solution into the volatile organic compound. In one embodiment this can be done with the water supply at the bottom of the carbon dioxide scrubber system. Introducing the $ClO_2$ solution into the volatile organic compound producing fermentation vessel is capable of reducing the concentration of VOC's.

FIG. 1 shows an air stream containing VOC's enters from line 102 into the $CO_2$ scrubber 104, this mixes with the liquid in the scrubber as it flows upward through the contacting chamber 106. The liquid in the scrubber 104 is drawn into the scrubber circulation pump 108 via line 110, the chlorine dioxide is delivered via line 112 and injected into line 110, this liquid is then pumped to the top of the scrubber 104 via line 114 where it flows downward through the contacting chamber 106 and reacts with the VOC's. The chlorine dioxide is produced by a generator 116.

While particular elements, embodiments and applications of the present invention have been shown and described, it will be understood, of course, that the invention is not limited thereto since modifications can be made by those skilled in the art without departing from the scope of the present disclosure, particularly in light of the foregoing teachings.

What is claimed is:

1. A method of treating volatile organic compounds produced during a fermentation process, the method comprising:
    producing a quantity of yeast product;
    generating $ClO_2$ gas wherein the $ClO_2$ gas produced is between 0.0005 and 5% by weight in air;
    dissolving said $ClO_2$ gas to form an aqueous $ClO_2$ solution having a concentration of about 3000 mg/L;
    introducing the aqueous $ClO_2$ solution into said quantity of yeast product; and
    fermenting the quantity of yeast product and aqueous $ClO_2$ solution;
    wherein said fermenting the quantity of yeast product and aqueous $ClO_2$ solution reduces volatile organic compounds produced.

2. The method of claim 1 wherein said steps are performed sequentially.

3. The method of claim 1 wherein said $ClO_2$ gas is generated by reacting chlorine gas with water and then adding sodium chlorite.

4. The method of claim 1 wherein said $ClO_2$ gas is generated by reacting sodium hypochlorite with an acid and then adding sodium chlorite.

5. The method of claim 1 wherein said $ClO_2$ gas is generated by reacting sodium chlorite and hydrochloric acid.

6. The method of claim 1 wherein said $ClO_2$ gas is generated using an electrochemical cell and sodium chlorite.

7. The method of claim 1 wherein said $ClO_2$ gas is generated using an electrochemical cell and sodium chlorate.

8. The method of claim 1 wherein said $ClO_2$ gas is generated using an equipment-based sodium chlorate and hydrogen peroxide method.

9. The method of claim 1 wherein said volatile organic compounds comprise at least one selected from the group consisting of acetyl aldehyde, acrolein, ethyl acetate, ethanol, and isoamyl alcohol.

10. The method of claim 1 wherein said aqueous $ClO_2$ solution is dosed at a concentration between about one and about 150 mg/L.

11. The method of claim 1 wherein said aqueous $ClO_2$ solution has an efficiency as $ClO_2$ in the stream of at least 90%.

12. A method of treating volatile organic compounds produced during a fermentation process, the method comprising:
    producing a quantity of yeast;
    introducing $ClO_2$ having an efficiency as $ClO_2$ of at least 90% into said quantity of yeast product; and
    fermenting the yeast product and $ClO_2$;
    wherein said fermenting the yeast product and $ClO_2$ reduces volatile organic compounds produced.

13. The method of claim 12 wherein said steps are performed sequentially.

14. The method of claim 12 wherein said volatile organic compounds comprise at least one selected from the group consisting of acetyl aldehyde, acrolein, ethyl acetate, ethanol, and isoamyl alcohol.

15. The method of claim 12 wherein said $ClO_2$ is an aqueous solution having a concentration between about one and about 150 mg/L.

16. The method of claim 12 wherein said $ClO_2$ is a gas.

17. The method of claim 12 wherein said $ClO_2$ is produced by reacting sodium chlorate and hydrogen peroxide.

18. The method of claim 12 wherein said $ClO_2$ is produced by dry mix chlorine dioxide packets having a chlorite precursor packet and an acid activator packet.

19. The method of claim 12 wherein said $ClO_2$ is generated using an electrochemical cell and sodium chlorite.

20. The method of claim 12 wherein said $ClO_2$ is generated using an electrochemical cell and sodium chlorate.

21. The method of claim 12 wherein said $ClO_2$ is generated using an equipment-based sodium chlorate and hydrogen peroxide method.

22. An apparatus for treating volatile organic compounds produced during a fermentation process, the apparatus comprising:
    (a) a $ClO_2$ generator comprising an inlet for introducing at least one chlorine-containing feed chemical and an outlet for exhausting a $ClO_2$ gas stream from said generator;
    (b) a batch tank fluidly connected to said $ClO_2$ generator outlet, said batch tank receiving said $ClO_2$ gas stream from said $ClO_2$ generator outlet, said batch tank comprising an inlet for introducing a water stream and an outlet for exhausting an aqueous $ClO_2$ solution from said batch tank; and
    (c) a volatile organic compound producing fermentation vessel fluidly connected to said batch tank, said volatile organic compound producing fermentation vessel receiving said aqueous $ClO_2$ solution from said batch tank;
    wherein introducing said ClO2 solution from said batch tank to said vessel reduces concentration of said volatile organic compounds.

23. The apparatus of claim 22 wherein said aqueous $ClO_2$ solution exhausted from said batch tank is dosed to a concentration between about one and about 150 mg/L.

24. The apparatus of claim 22 wherein said volatile organic compound producing fermentation vessel is a carbon dioxide scrubber.

25. The apparatus of claim 24 wherein said aqueous $ClO_2$ solution in introduced at the bottom of said carbon dioxide scrubber or regenerative thermal oxidizer.

26. The apparatus of claim 22 where said volatile organic compound is selected from the group consisting of acetyl aldehyde, acrolein, ethyl acetate, ethanol, or isoamyl alcohol.

* * * * *